(12) United States Patent
Aki

(10) Patent No.: US 8,178,295 B2
(45) Date of Patent: May 15, 2012

(54) ANALYTE EVALUATION APPARATUS

(75) Inventor: Michihiko Aki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 797 days.

(21) Appl. No.: 12/054,810

(22) Filed: Mar. 25, 2008

(65) Prior Publication Data

US 2008/0237041 A1 Oct. 2, 2008

(30) Foreign Application Priority Data

Mar. 26, 2007 (JP) .................................. 2007-79021

(51) Int. Cl.
*C12M 1/34* (2006.01)
*G01N 33/52* (2006.01)
*G01N 33/68* (2006.01)
*G01N 21/66* (2006.01)

(52) U.S. Cl. .... 435/6.1; 436/172; 436/518; 204/403.01; 435/287.2

(58) Field of Classification Search ......... 204/403.01–403.15; 205/775, 205/777.5, 778, 792; 436/6, 86, 172, 94, 436/518; 435/7.1, 287.1, 287.2, 6.1
See application file for complete search history.

(56) References Cited

U.S. PATENT DOCUMENTS

| 6,051,124 A | 4/2000 | Aoki |
| 2003/0087296 A1* | 5/2003 | Fujita et al. ........................ 435/6 |
| 2005/0069932 A1* | 3/2005 | Arinaga et al. ................... 435/6 |
| 2006/0003437 A1* | 1/2006 | Fujihara et al. ............ 435/287.1 |

FOREIGN PATENT DOCUMENTS

| JP | 10-104188 A | 4/1998 |
| JP | 10-141562 A | 5/1998 |

OTHER PUBLICATIONS

Skoog et al., Principles of Instrumental Analysis, Fifth Edition, pp. 22-23 and 572-576.*
Nishizawa, Kazuki et al., "The Construction of Biointerfaces for μTAS," Bio Industry, vol. 24, No. 2., pp. 12-19.
Kaji, Noritada et al., "Microfluidic Devices for Genetic Analysis," Bio Industry, vol. 24, No. 2, pp. 20-24.
Wakida, Shin-ichi et al., "Microfluidic Point of Care Testing Biochip for Stress Marker," Bio Industry, vol. 24, No. 2., pp. 37-43.

* cited by examiner

*Primary Examiner* — Jeffrey T Barton
*Assistant Examiner* — Jennifer Dieterle
(74) *Attorney, Agent, or Firm* — Westerman, Hattori, Daniels & Adrian, LLP

(57) ABSTRACT

This analyte evaluation apparatus has an analyte space for holding a liquid containing an analyte, a working electrode, a counter electrode and a reference electrode, and the potential of the working electrode is altered with respect to the potential of the reference electrode as the standard potential, and the behavior of the analyte is observed to thereby evaluate the analyte, and the working electrode is provided in the analyte space and the counter electrode and reference electrode are provided in an electrode medium container for holding an electrically conductive electrode medium while being connected via an electrically conductive communicating part for substantially blocking the passage of liquid from the analyte space.

5 Claims, 5 Drawing Sheets

ANALYTE EVALUATION APPARATUS

CROSS-REFERENCE TO RELATED APPLICATIONS

This application is based upon and claims the benefit of priority from the prior Japanese Patent Application No. 2007-79021, filed on Mar. 26, 2007, the entire contents of which are incorporated herein by reference.

BACKGROUND OF THE INVENTION

1. Field of the Invention

The present invention relates to an analyte evaluation apparatus which has an analyte space for holding a liquid containing an analyte that includes a protein or the like (hereunder the liquid being sometimes called an analyte solution), a working electrode, a counter electrode and a reference electrode, and in which the potential of the working electrode is altered with respect to the potential of the reference electrode as the standard potential (that is, the potential difference between the working electrode and reference electrode is altered with respect to the potential of the reference electrode as the standard potential), and the behavior of the analyte is observed to thereby evaluate the analyte. When the analyte includes a protein or the like, this apparatus is simply called a voltage-driven protein sensor or voltage-driven protein chip. Consequently, the analyte evaluation apparatus of the embodiments in this specification can sometimes be called a voltage-driven analyte sensor or voltage-driven analyte chip.

2. Description of the Related Art

Voltage-driven protein chips are of interest because they can detect a wide variety of proteins rapidly and with high sensitivity, and since they are usually small enough to be held in the palm of the hand, they are easily applicable to medical settings and inspections (see for example Yoshinobu BABA, "Nihon no biokei μ-TAS saishin gijutsu" (Biological μ-TAS latest technologies in Japan), Bioindustry Tokushugo (exclusive reports), 2007, Vol. 24(2), p. 5-78).

The typical structure of a voltage-driven protein chip can be explained for example as follows. A nucleotide probe, which is a nucleotide having bound thereto a target protein and a fluorescent dye or other fluorescent label, is fixed via a thiol group for example to a working electrode made of a metal gold film for example. The nucleotide probe is usually negatively charged, and applying a rectangular wave potential (for example, ±200 mV) to the working electrode causes the nucleotide probe to stand up from the working electrode by electrostatic repulsion or lie down on the working electrode by electrostatic attraction.

This movement is called the switching movement of the nucleotide probe. If the nucleotide probe is exposed to excitation light from an argon ion laser for example to excite the fluorescent label when the nucleotide probe is standing and elongated, fluorescent light is emitted, while almost no light is emitted (that is, the probe is quenched) if the fluorescent label is excited in the same way when the nucleotide probe is lying down and/or contracted. The fluctuation range of the fluorescent intensity due to repeated lighting (that is emission) and quenching of the fluorescent label is called the fluorescent intensity switching amplitude.

If the cycle of the potential applied to the working electrode is as low as 0.5 Hz, the switching movement of the nucleotide probe will be synchronized with the cycle of the potential. However, if the cycle is as high as 1 kHz or higher for example, the switching movement of the nucleotide probe will not be able to follow the cycle of the potential, and the fluorescent intensity switching amplitude will decline, while the rising and falling parts of the rectangular waveform will become more gentle. This change in the waveform is called decreased frequency responsiveness. Moreover, when the nucleotide probe is bound to a protein the mass is much greater than the mass of the nucleotide probe without the protein (10 times more for example), causing the switching movement of the nucleotide probe no longer to be able to follow the cycle of the potential, resulting in a decrease in fluorescent intensity switching amplitude and decreased frequency responsiveness. Furthermore, because of the short distance (a few to 100 nm for example) between the fluorescent dye and the protein bound to the nucleotide probe, the protein absorbs (quenches) the fluorescence, also causing a decrease in fluorescent intensity switching amplitude.

In a voltage-driven protein chip, it is possible to determine the presence or absence, or type of a target protein bound to the nucleotide probe or to measure its concentration with high sensitivity based on such decreases in fluorescent intensity switching amplitude and frequency responsiveness. Although a voltage-driven protein chip was explained above, the above explanation can be applied to a voltage-driven analyte chip or to any analyte evaluation apparatus described in this specification. In this case, the element including the fluorescent label and responding part with the analyte can be seen as corresponding to the nucleotide probe described above. An element including a fluorescent part and a responding part with an analyte in this way is sometimes simply called a probe hereunder.

In the embodiments described in this specification, "evaluating an analyte" means determining the presence or absence, type and/or concentration of an analyte as discussed above, and an "analyte" is a substance to be evaluated in this way, such as a protein for example, which may or may not include parts having the function of enabling evaluation, such as the aforementioned fluorescent label or the aforementioned part that may be standing and/or elongated, or lying down and/or contracted (hereunder sometimes called the responding part) or parts having the function of binding to the working electrode (such as a thiol group). When the analyte does not include these elements, they are added to the analyte or to the working electrode at certain stages up to evaluation.

A counter electrode and reference electrode are necessary for applying voltage to the working electrode. In a voltage-driven analyte chip, the probability at which the analyte collides with the working electrode is much greater (about 100 times greater for example) if these electrodes are incorporated into a small channel (such as about 0.5 mm in height, 2.5 mm in width, 50 mm in length) than in a system in which the solution is simply agitated in a 50 mL beaker for example, allowing for more rapid evaluation.

However, in such a voltage-driven analyte chip bubbles may occur in the analyte solution as it flows through the channel, and when these bubbles pass over the electrodes or are present between electrodes, they may impede electrical conduction between the working electrode and counter electrode or between the working electrode and reference electrode, making it difficult to accurately apply the desired potential difference between the working electrode and reference electrode. As a result, not only can the behavior of the analyte not be detected accurately, but if an excessively large potential difference is applied the probe may become desorbed from the working electrode or become oxidized, and there will be no switching movement signal to be observed among other problems. These bubbles are believed to occur due to pressure changes and/or temperature changes in the channel, which reduce the solubility of gasses in the analyte solution in the channel. This problem was explained with reference to an analyte solution flowing in a channel, but may occur even when the analyte solution is retained in the analyte space rather than flowing in a channel.

When conduction between electrodes is broken due to bubbles, one possible means of dealing with the problem is to break the application of voltage in the circuit, but this is not easy for the following reasons. For example, the applied voltage needs to be broken before ion rearrangement occurs around the electrodes, but even if the applied voltage is greater than ±500 mV, if the circuit is not broken within a few hundred nanoseconds with overshoot controlled within 100 mV, the probe may become desorbed from the working electrode or the probe adsorbed on the working electrode may become oxidized so there is no switching signal to observe. However, such a circuit is not easy to achieve.

Another possible method of preventing bubbles would be to first degas the liquid with a degassing unit before supplying it to the channel, but it would still be difficult to completely prevent bubbling.

Bubbles are less likely to occur in a liquid if the liquid is made to flow in the channel by application of pressure rather than suction, but leakage from the channel then becomes more likely, and the structure of the unit is complicated by the measures taken to prevent leakage, detracting from productivity when the apparatus is produced.

SUMMARY OF THE INVENTION

According to an aspect of an embodiment, there is an analyte evaluation apparatus which includes: an analyte space for holding a liquid containing an analyte; a working electrode; a counter electrode; and a reference electrode, and in which the potential of the working electrode is altered with respect to the potential of the reference electrode as the standard potential and the behavior of the analyte is observed to thereby evaluate the analyte, wherein:

one or more of the working electrodes are provided in the analyte space;

one or more of the counter electrodes and one or more of the reference electrodes are provided; and at least one of the counter electrodes and reference electrodes is provided in an electrode medium container which holds an electrically conductive electrode medium and which is connected via an electrically conductive communicating part that substantially blocks the passage of the liquid from the analyte space.

According to another aspect of an embodiment, there is an analyte evaluation apparatus which comprises: an analyte space for holding a liquid containing an analyte; a working electrode; a counter electrode; and a reference electrode, and in which the potential of the working electrode is altered with respect to the potential of the reference electrode as the standard potential and the behavior of the analyte is observed to thereby detect the analyte, wherein:

one or more of the working electrodes are provided in the analyte space;

one or more of the counter electrodes and one or more of the reference electrodes are provided;

at least one of the counter electrodes and reference electrodes is provided in an electrode medium container which holds an electrically conductive electrode medium and which is provided independently from the analyte space; and at least one of the working electrodes and a lead thereof has an auxiliary electrode that is exposed inside the electrode medium container.

DESCRIPTION OF THE PREFERRED EMBODIMENTS

Embodiments of the present invention are explained below using drawings, examples and the like. These drawings, examples and the like and explanations are given as examples of the present invention, and are not meant to restrict the scope of the invention. Other embodiments may of course be included in the present invention to the extent that they are consistent with its intent. The same symbols indicate the same elements in all drawings.

Interference with electrical conduction between the working electrode and counter electrode and between the working electrode and reference electrode can be prevented by means of the structure in the above-mentioned summary even when bubbles occur in the analyte solution.

In this case, it may be desirable that neither the working electrode nor its lead have any part that is exposed inside the electrode medium container. "Exposed inside the electrode medium container" means being physically inside the electrode medium container and electrically connected to the electrode medium.

Figure 1:
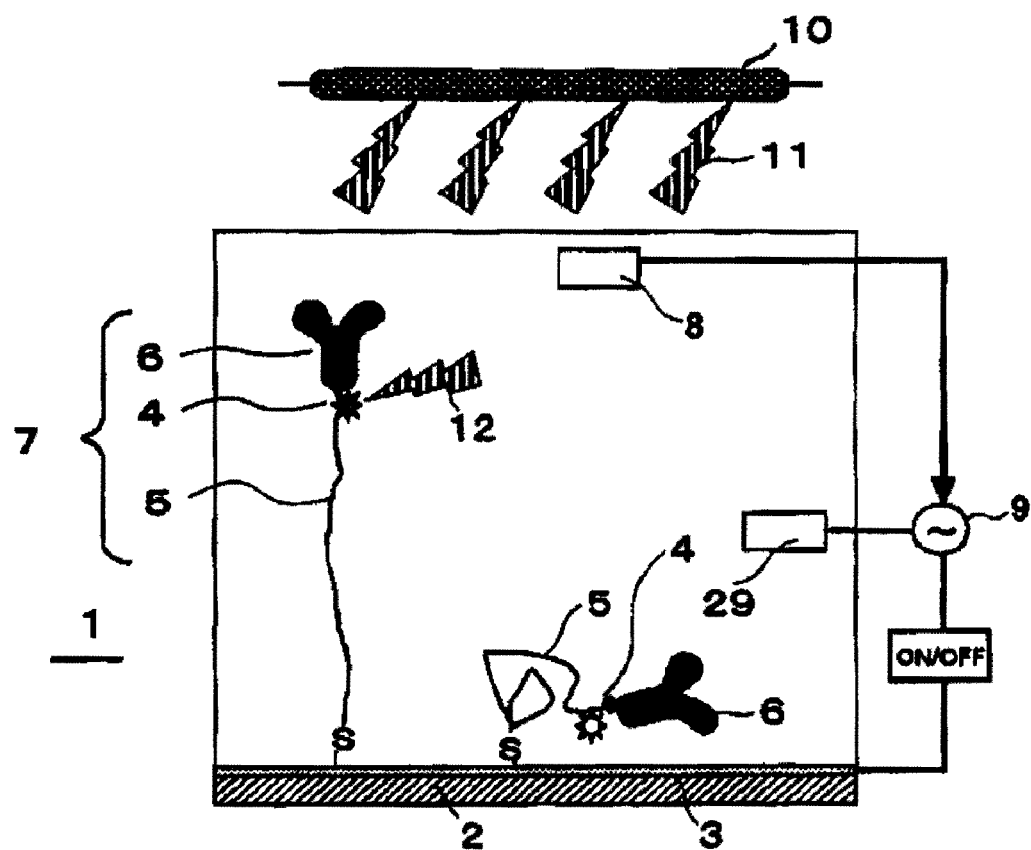
FIG. 1 schematically shows two analytes bound to a working electrode in an elongated and light-emitting state and contracted and quenched state, respectively.

The structure of an embodiment described in this specification is explained below using FIGS. 1 through 5. FIG. 1 schematically shows an example of the behavior of an analyte in an analyte evaluation apparatus of one embodiment described in this specification.

In the analyte evaluation apparatus 1 in FIG. 1, analyte 6 is bound via fluorescent label 4 and responding part 5, which has either a natural single-stranded oligonucleotide structure, a natural or artificial double-stranded nucleotide body partially having a single-stranded part or a natural or artificial double-stranded nucleotide body, on working electrode 3 on substrate 2 (corresponding to the base structure described below). The S below the single-stranded oligonucleotide structure indicates that the responding part 5 is bound directly to working electrode 3 by means of a thiol group. If a part that reacts specifically with analyte 6 is provided at the end of responding part 5, only an analyte that reacts specifically with the responding part will be captured by the responding part when an analyte solution is brought into contact with an analyte evaluation apparatus having such a responding part 5 and fluorescent label 4. Fluorescent label 4, responding part 5 and analyte 6 may together be called nucleotide probe 7.

In a structure assembled in this way, the analyte is in a resting, contracted state on working electrode 3 when a specific potential difference is not being applied between working electrode 3 and reference electrode 8. When a specific potential difference is applied by external field-application unit 9 between working electrode 3 and reference electrode 8, this resting, contracted nucleotide probe 7 becomes standing and elongated. The standing, elongated nucleotide probe 7 is shown on the left in FIG. 1, while the resting, contracted nucleotide probe 7 is shown on the right.

Fluorescence 12 is obtained when the standing, elongated probe is exposed to light 11 from light irradiation unit 10. However, the fluorescence disappears when the analyte is in a resting and contracted position. Thus, the analyte can be evaluated by observing this fluorescence emission and quenching behavior. For example, when a rectangular wave potential difference is provided between working electrode 3 and reference electrode 8, and the response behavior of fluorescence emission and quenching is observed, the frequency responsiveness is less when an analyte is captured on the working electrode (more specifically when it is captured by the responding part of the working electrode) than when it is not captured (more specifically, when it is not captured by the responding part on the working electrode). Since the reaction between the responding part and the analyte is specific, the type of analyte can be determined according to whether or not it has been captured. The amount (concentration or population) of an analyte can also be determined because the decrease in frequency responsiveness or switching amplitude is greater the greater the number captured.

Figure 2:
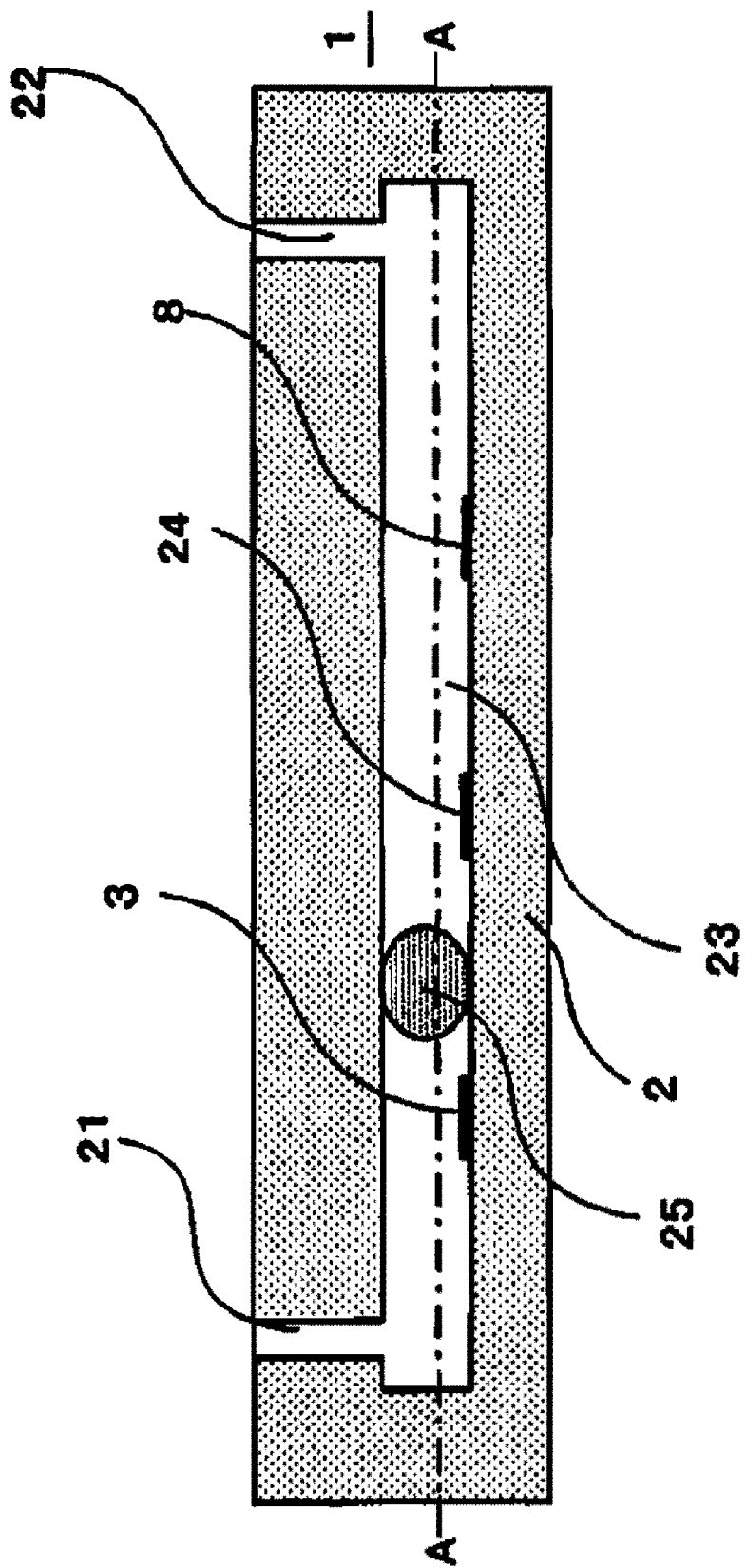
FIG. 2 is a schematic side view of a conventional type of analyte evaluation apparatus.
Figure 3:
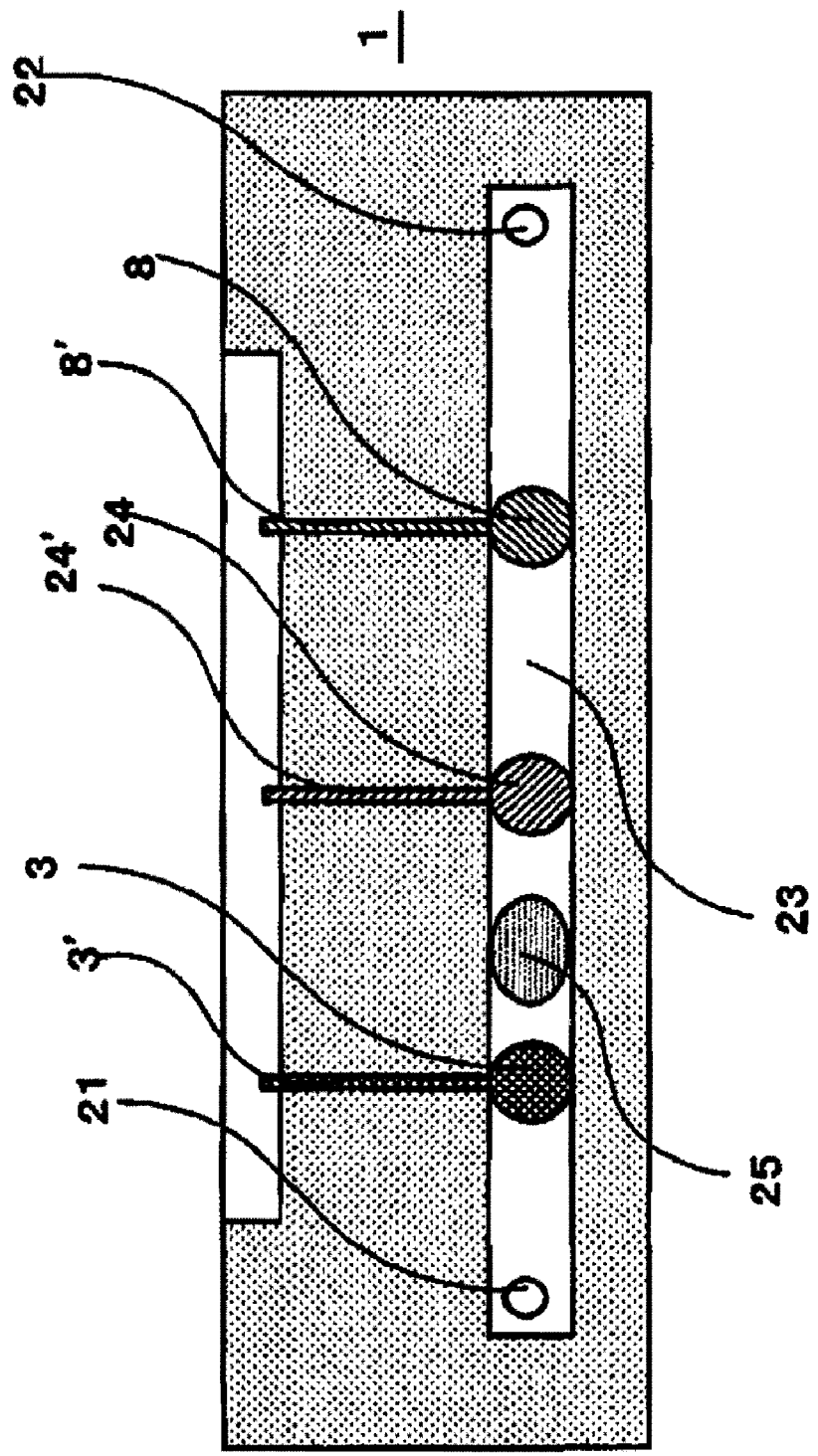
FIG. 3 is a cross-section on the A-A plane in FIG. 2.
Figure 4:
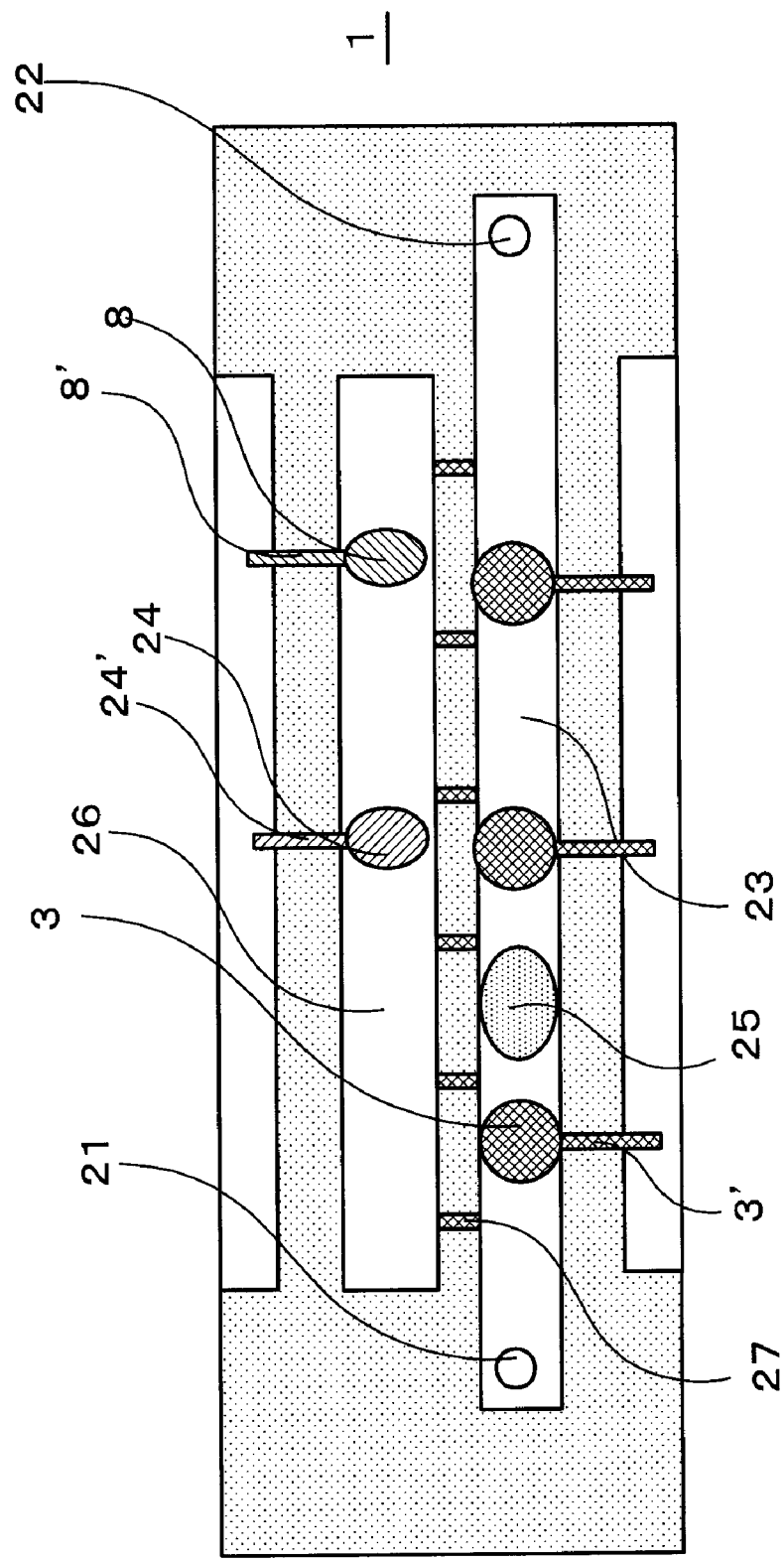
FIG. 4 is a schematic cross-section as in FIG. 3 but showing an embodiment of the invention.

FIG. 2 is a model side view of a conventional analyte evaluation apparatus (voltage-driven analyte chip), while FIG. 3 shows a model cross-section of the part below the A-A plane in FIG. 2 as seen from above, and FIG. 4 shows a similar model cross-section of one embodiment described in this specification.

The conventional type of voltage-driven analyte chip has analyte space 23 with analyte inlet 21 and outlet 22 on base structure 2, and working electrode 3, counter electrode 24 and reference electrode 8 on the surface of analyte space 23. Often there are more than one of each of these electrodes. In particular, it is often advantageous to have multitude of working electrodes because this allows many analytes to be captured. If an analyte solution is supplied under these conditions and bubbling occurs, bubbles 25 may cover the electrodes or intervene between electrodes as shown in FIGS. 2 and 3, creating problems by blocking electrical conduction between the working electrode and counter electrode and between the working electrode and reference electrode. 3', 8' and 24' represent the leads for working electrode 3, reference electrode 8 and counter electrode 24, respectively.

By contrast, as shown in FIG. 4 for example, the structure of one embodiment described in this specification has electrode medium container 26 inside analyte evaluation apparatus 1, with electrically conductive communicating parts 27 substantially blocking the passage of analyte liquid from analyte space 23 to electrode medium container 26, and at least one of counter electrode 24 and reference electrode 8 contained in electrode medium container 26. Since in this structure there is no particular advantage to leaving a counter electrode 24 or reference electrode 8 in analyte space 23, usually all of these electrodes are contained in electrode medium container 26.

With this structure, even if a bubble 25 occurs in analyte space 23 the electrical conduction between the working electrode and counter electrode or between the working electrode and reference electrode is maintained via electrically conductive communicating parts 27 as long as not all of these electrically conductive communicating parts are blocked by bubbles, thereby averting the problems of prior art. A plurality of electrically conductive communicating parts can be provided, and the more they are provided, the greater the security against bubbles.

In this structure, when there are many electrically conductive communicating parts it is advantageous for leads 3' of the working electrodes to be on the opposite side from electrically conductive communicating parts 27 in analyte space 23 as shown in FIG. 4. More working electrodes can also be provided because the reference electrode and counter electrode are elsewhere.

Rather than the working electrode and its lead having no parts that are exposed in the electrode medium container as in FIG. 4, it may also be useful that at least either the working electrode or its lead is exposed in the electrode medium container. In this case, because part of the function of the working electrode itself is within the electrode medium container 26, even if all of electrically conductive communicating parts 27 become blocked by bubbles the electrical connection of working electrode 3 with reference electrode 8 and counter electrode 24 is maintained via lead 3'.

Figure 5:
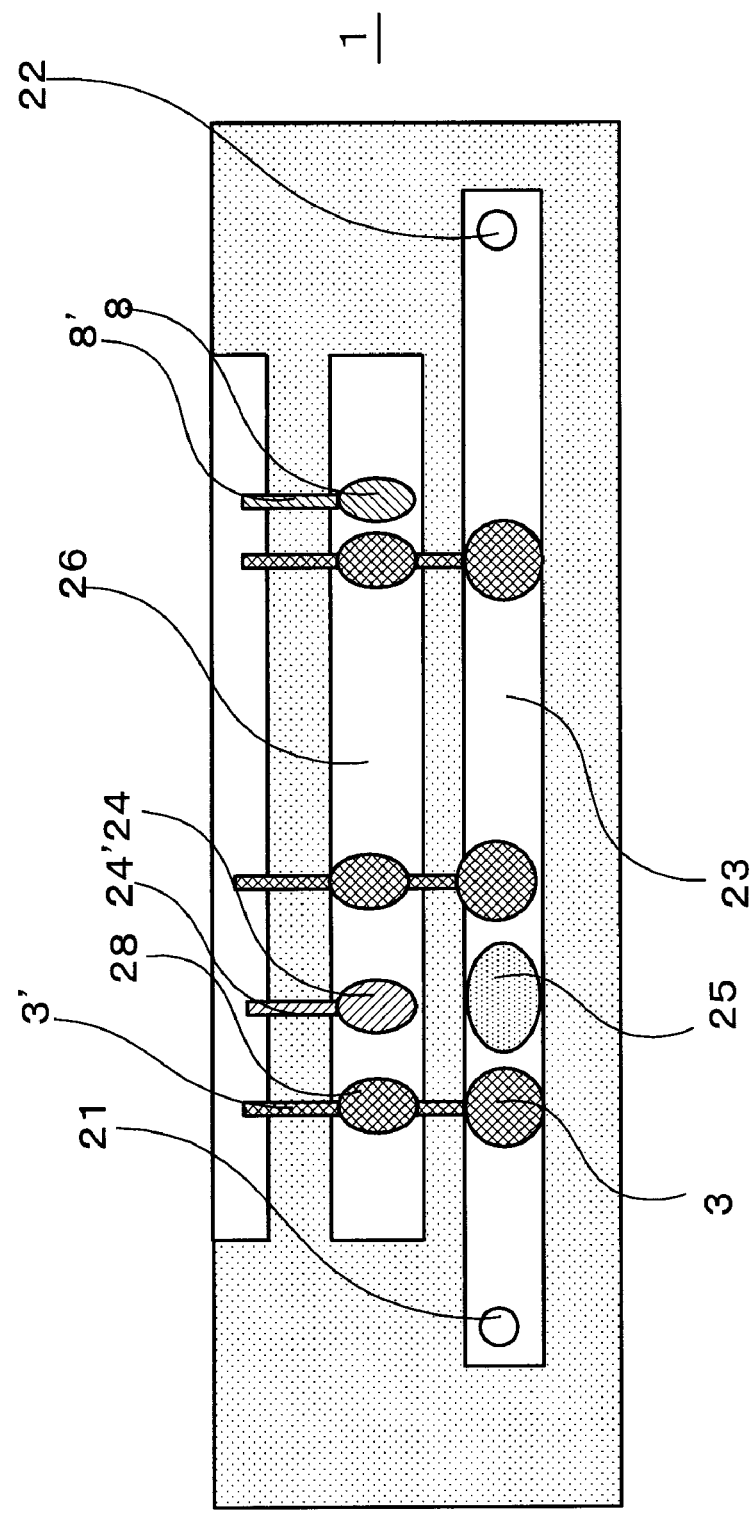
FIG. 5 is a schematic cross-section as in FIG. 3 but showing another embodiment of the invention.

Such a structure can be achieved by changing the arrangement of the working electrode lead in the structure of FIG. 4, but since electrically conductive communicating parts 27 are functionally no longer necessary, a structure such as that shown in FIG. 5 is advantageous.

FIG. 5 is a model cross-section similar to that of FIG. 3. In FIG. 5, part of the lead of working electrode 3 is provided inside electrode medium container 26 as auxiliary electrode 28. There are no electrically conductive communicating parts 27, and analyte space 23 and electrode medium container 26 are separated by a wall to form independent spaces. In this way, part of the function of the working electrode itself is inside electrode medium container 26, making it easier to avoid problems due to bubbles. This is also more advantageous than in FIG. 4 because there are no electrically conductive communicating parts.

In the embodiments described in this specification, the analyte space for holding the analyte solution, the base structure, the working electrode, counter electrode and reference electrode and all other parts which are not explained in these Specifications are not particularly limited, and materials and structures similar to those of a conventional analyte evaluation apparatus may be used.

The analyte space may be one through which the analyte solution flows as in a voltage-driven analyte chip, or may be in the form of a beaker. In the case of a voltage-driven analyte chip, the channel is usually a few to tens of mm long, 1 to 10 mm wide and about 0.01 to 10 mm deep.

Glass, sapphire, silicon, ceramic, plastic or the like can be used for the base structure.

It is often desirable to use gold for the working electrode because this facilitates bonding via thiol groups or the like. The auxiliary electrode may be prepared from the same or similar materials as either the working electrode or counter electrode, without limitations.

The working electrode, counter electrode and reference electrode are not particularly limited as to shape, but are often in disc form. The same applies to the auxiliary electrode. Assuming disc-shaped electrodes about 2 mm in diameter, the numbers of working electrodes, counter electrodes and reference electrodes in a channel-type analyte space are obviously limited due to the space limitation.

In the embodiments described in this specification, any technology can be adopted for the method of altering the potential of the working electrode with respect to the potential of the reference electrode as the standard potential, and for the structural parts therefor, without any particular limitations. A rectangular wave or sine wave can be used for altering the potential difference, but a rectangular wave is convenient for practical reasons.

It is desirable to use fluorescence as described above for "observing the behavior of the analyte" in the embodiments described in this specification, but this is only one example of observing the behavior of the analyte in the analyte evaluation apparatus of the embodiments described in this specification, and other methods such as electrical response behavior observation could be used for example. The analyte evaluation apparatus for the embodiments described in this specification is not particularly limited by the method of observing the behavior of the analyte. In this case, "observing the behavior of the analyte" includes not only observing the behavior of the analyte itself but also observing the behavior of the analyte indirectly through the behavior of a part contained in the analyte or a part auxiliary to the analyte. One example of observing the behavior of the analyte indirectly through the behavior of an auxiliary part is a case in which the probe is made up of an analyte, a fluorescent label and a responding part, and the emission and quenching of fluorescence of the fluorescent label due to extension/contraction of the responding part is observed.

An electrically conductive communicating part for the embodiments described in this specification may be any that substantially blocks passage of the analyte solution from the analyte space into the electrode medium container, and which allows electrical connection between the analyte space and the electrode medium container. It may be an organic or inorganic substance, and may be a porous body. It may also be filled with a highly viscous medium that easily blocks the passage of the analyte solution through the porous body. Examples include those containing KCl and agar, structures commonly called salt bridges and similar structures. "Substantially" here means that slow passage is permissible to the extent that it does not inhibit actual observation of the behavior of the analyte, which is the object of the embodiments described in this specification.

The shape of the electrically conductive communicating part for the embodiments described in this specification is not particularly limited. A plurality of electrically conductive communicating parts may be provided as shown in FIGS. 4 and 5. The cross-section is usually circular, but other shapes are possible. The electrically conductive communicating part may constitute almost the whole of the wall separating the analyte space from the electrode medium container. In this case, the electrically conductive communicating part may be in the form of a sheet.

The electrode medium container of an embodiment described in this specification is filled with electrode medium. The electrode medium is a medium for electrically connecting the counter electrode and/or reference electrode with the working electrode, and may be any that is suited to this purpose. Examples include an aqueous salt solution and a highly viscous substance containing a salt and agar. When the electrically conductive communicating part is a communicating medium containing KCl and agar, the electrode medium may be an aqueous KCl solution.

The electrode medium is preferably used in a degassed state in order to prevent bubbling in the electrode medium container.

The shape of the electrode medium container is not particularly limited. It may be open to the outside, but since the medium does not need to be frequently replaced, it is often preferable that the electrode medium be sealed filling the electrode medium container. This is to prevent contamination by bubbles. This is particularly desirable when using a degassed electrode medium.

In the embodiments described in this specification, as explained above, an "analyte" is usually a substance to be evaluated such as a protein for example, and may or may not include a part having a function that enables evaluation, such as a part (for example, a thiol group) having the function of binding to the fluorescent label, responding part or working electrode. Thus, the analyte of FIG. 1 is only an example of an analyte for the embodiments described in this specification. As explained above, the part for binding to the working electrode may already be present in the analyte or may be provided in advance on the working electrode. The same applies to the responding part and fluorescent label. When the responding part or the part for binding to the working electrode is already provided on the working electrode, the analyte needs to have a structural part for binding to those parts. For this reason, "binding between the analyte and the working electrode" in the embodiments described in this specification includes cases in which the analyte is bound to the working electrode via the responding part or the part for binding on the working electrode. This "binding" may be chemical binding (a covalent bond or ion bond for example), biological binding (DNA complement chain binding, binding between proteins) or physical binding (adsorption for example).

The analyte of the embodiments described in this specification may be any capable of binding to the working electrode in this way, but since it is easier to identify the type of analyte if binding between the analyte and working electrode is specific, the analyte preferably includes a part consisting of at least one substance selected from the group consisting of proteins, DNA, RNA, antibodies, natural or artificial single-stranded nucleotide bodies, natural or artificial double-stranded nucleotide bodies partially having a single-stranded part, natural or artificial double-stranded nucleotide bodies, aptamers, products of limited degradation of antibodies with proteolytic enzymes, organic compounds and complexes having affinity for proteins, biopolymers having affinity for proteins, and complexes and any combinations of these. In particular, it preferably includes a part consisting of a protein that is in particular demand. In the embodiments described in this specification, a nucleotide body is a polynucleotide or oligonucleotide.

The aforementioned "products" are produced by limited degradation of antibodies with proteolytic enzymes, and may include antibody Fab fragments or $(Fab)_2$ fragments, fragments derived from antibody Fab fragments or $(Fab)_2$ fragments, and derivatives of these and the like as long as these are consistent with the intent of the embodiments described in this specification.

Monoclonal immunoglobulin IgG antibodies for example can be used as the antibodies. IgG antibody Fab fragments or $(Fab)_2$ fragments can be used as fragments derived from IgG antibodies. Fragments derived from such Fab fragments or $(Fab)_2$ fragments may also be used.

Examples of organic compounds having affinity for proteins that can be used include butanic acid, pyruvic acid, tyrosine and other enzyme substrates and analogues, nicotinamide adenine dinucleotide (NAD) and other co-enzymes and diethylstilbestrol, brimonidine tartrate, 9-cis retinoic acid and other agonists and tetrodotoxin, naloxone, 6-mercaptopurine and other antagonists and the like.

An example of a complex having affinity for proteins that can be used is nitro-triacetic acid (NTA), a complex that binds to the complexing sites of proteins (such as amino acid sequences formed by repeating histidine residues).

A biological polymer having affinity for a protein may be a protein that acts as a protein substrate or catalyst, or constituent proteins making up a molecular complex.

The analyte evaluation apparatus for the embodiments described in this specification must comprise the aforementioned analyte space, working electrode, counter electrode, reference electrode and electrode medium container, as well as an electrically conductive communicating part and auxiliary electrode in some embodiments, but other parts explained above and other parts that were not explained may be considered to be either included or not included. For example, those in which the electrically conductive communicating part contains no salt bridge or other medium for preventing the passage of analyte solution, in which the electrode medium container contains no electrically conductive electrode medium, and in which no part for binding to the analyte is formed on the working electrode are all included in the scope of the analyte evaluation apparatus for the embodiments described in this specification.

EXAMPLES

Examples and comparative examples of the invention are explained next.

Comparative Example 1

A voltage-driven analyte chip was prepared with the structure shown in FIGS. 2 and 3. Specifically, an analyte space 50 mm long, 2.5 mm wide and 0.5 mm high was formed in a PDMS (polydimethylsiloxane) base structure, and three working electrodes (gold, dia. 2 mm), four counter electrodes (platinum, dia. 2 mm) and one reference electrode (silver, dia. 2 mm) were provided.

A fluorescent label and a responding part having a natural double-stranded oligonucleotide structure were provided via a thiol group on the working electrode as shown in FIG. 1. A part reacting specifically with the analyte was provided at the end of the responding part.

A buffer solution (10 mM Tris-HCl, pH 7.4, 50 mM NaCl) of a protein as the analyte was made to flow through this voltage-driven analyte chip at a rate of 100 µL per minute, a rectangular wave potential difference was provided between the working electrode and the reference electrode with respect to the potential of the reference electrode as the standard potential, and light was supplied from outside. Then, fluorescent emission and quenching were observed.

Under these conditions, bubbles began to appear in the analyte space after about 5 minutes, and the potential difference reached 15,000 mV. After the bubbles had passed through the analyte space, fluorescence emission and quenching was not observed even when rectangular wave potential was applied to the working electrode.

Example 1

A voltage-driven analyte chip was prepared with the structure of FIG. 4. The material of the base structure, the size of the analyte space, and the material, size and numbers of the working electrodes, counter electrodes and reference electrode were all as in the comparative example.

However, as shown in FIG. 4, an electrode medium container 50 mm long, 2.5 mm wide and 0.5 mm high was provided, and the counter electrodes and reference electrode were contained therein. The analyte space and electrode medium container were 5 mm apart, and were connected by 4 salt bridges each 1 mm in diameter. The salt bridges were filled with a composition of KCl and agar. The electrode medium container was filled in advance with a degassed 3 M aqueous solution of KCl, and the opening was then sealed.

A fluorescent label and a responding part having a natural double-stranded oligonucleotide structure were provided on the working electrode as in Comparative Example 1 as shown in FIG. 1. A part reacting specifically with the analyte was provided at the end of the responding part.

A buffer solution (10 mM Tris-HCl, pH 7.4, 50 mM NaCl) of a protein as the analyte was made to flow through this voltage-driven analyte chip at a rate of 100 µL per minute as in Comparative Example 1, a rectangular wave potential difference was provided between the working electrode and the reference electrode, and light was supplied from outside. Then, fluorescent emission and quenching were observed.

Under these conditions, no electrically conductive problem due to bubbles was observed in the analyte space even after about 10 minutes, and no abnormalities were observed in the applied potential difference.

What is claimed is:

1. An analyte evaluation apparatus which comprises: an analyte space for holding a liquid containing an analyte; a working electrode; a counter electrode; and a reference electrode, and in which the potential of said working electrode is altered with respect to the potential of said reference electrode as a standard potential and the behavior of said analyte is observed to thereby detect said analyte, wherein:
   one or more of said working electrodes are provided in said analyte space;
   one or more of said counter electrodes and one or more of said reference electrodes are provided;
   at least one of said counter electrodes and said reference electrodes is provided in an electrode medium container which holds an electrically conductive electrode medium and which is provided independently from said analyte space;
   at least one of said working electrode and a lead thereof has an auxiliary electrode that is exposed inside said electrode medium container; and
   wherein said analyte comprises a fluorescent label capable of emitting fluorescence in response to received light when the distance between said fluorescent label and said working electrode increases, and said behavior of said analyte is emission and/or quenching behavior of said fluorescence.

2. The analyte evaluation apparatus according to claim 1, comprising a plurality of said working electrodes.

3. The analyte evaluation apparatus according to claim 1, wherein every one of said at least one of said counter electrodes and said reference electrodes is provided inside said electrode medium container.

4. The analyte evaluation apparatus according to claim 1, wherein said electrode medium is degassed, and is sealed filling said electrode medium container.

5. The analyte evaluation apparatus according to claim 1, wherein said analyte includes a part comprising at least one substance selected from said group consisting of proteins, DNA, RNA, antibodies, natural or artificial single-stranded nucleotide bodies, natural or artificial double-stranded nucleotide bodies partially having a single-stranded part, natural or artificial double-stranded nucleotide bodies, aptamers, products obtained by limited degradation of antibodies with proteolytic enzymes, organic compounds and complexes having affinity for proteins, biopolymers having affinity for proteins, and complexes and any combinations thereof.

* * * * *